United States Patent [19]

Toda et al.

[11] Patent Number: 5,306,844
[45] Date of Patent: Apr. 26, 1994

[54] TARTARIC ACID AMIDE DERIVATIVE AND METHOD OF PRODUCING THE SAME

[75] Inventors: Fumio Toda; Koichi Tanaka, both of Ehime, Japan

[73] Assignee: Mitsubishi Gas Chemical Company, Inc., Tokyo, Japan

[21] Appl. No.: 522,065

[22] Filed: May 11, 1990

Related U.S. Application Data

[63] Continuation of Ser. No. 215,023, Jul. 5, 1988, abandoned.

[30] Foreign Application Priority Data

Jul. 6, 1987 [JP]   Japan .................................. 62-166933

[51] Int. Cl.⁵ .......................................... C07C 235/06
[52] U.S. Cl. .................................. 564/160; 564/155; 564/158; 564/159; 549/450
[58] Field of Search ............... 564/155, 158, 159, 160, 564/352; 549/450

[56] References Cited

PUBLICATIONS

Seebach et al, Chemical Abstracts, 99: 87600m (1983).
Behr et al, Chemical Abstracts, 94: 139766p (1981).
Fukutani et al, Tetrahedron Letter, 25, No. 51, pp. 5911-5912 (1984).
Toda et al, Chemistry Letters, pp. 113-116 (1986).
Toda et al, Chemistry Letters, pp. 1901-1912 (1986).
Toda et al, Chemistry Letters, pp. 1393-1396 (1987).
"Japanese Patent Appln. Laid-Open No. SHO 58-150526", *Chemical Abstracts;* vol. 100, p. 549, 1984.
"Japanese Patent Appln. Laid-Open No. SHO 60181033", *Chemical Abstracts;* vol. 104, p. 682, 1986.
"Japanese Patent Appln. Laid-Open No. SHO 61207363", *Chemical Abstracts;* vol. 106, p. 592, 1987.
"Asymmetric Synthesis Via Axially Dissymmetric Molecules. A Binaphthol-Modified Complex Aluminum Hydride Reagent Processing Extremely High Ability of Chiral Recognition", *Pure & Appl. Chem.*, vol. 53, pp. 2315-2322, 1981 (Noyori).
Nishizawa et al–"Asymmetric Synthesis of Chiral Geraniol-1-d and Related Terpenic Alcohols" Tetrahedron Letters, vol. 21, pp. 2821-2824 1980.
Nishizawa et al–"Highly Enantioselective . . . " *Tetrahedron Letters*, vol. 22, pp. 247-250 Pergamon Press Ltd. (1981).
Seebach et al–"Herstellung von Hilfsstoffen . . . " *Helvetica Chimica Acta*, vol. 60, pp. 301-325 (1977).
Felner et al–"Totalsynthese des Antibioticums Anisomycin" *Hevetica Chimica Acta*, vol. 53, pp. 754-763 (1970).
Toda–European Patent Appln. EP 198 202, as abstracted in *Chemical Abstracts*, vol. 106, p. 619 (1987).
Noyori et al–"A Highly Efficient Synthesis of Prostaglandin Intermediates Possessing the 15S Configuration" *American Chemical Society*, No. 101, pp. 5843-5844 (1979).
Achmatowicz et al., "Tetrahedron Letters", vol. 28, No. 26, pp. 2999-3002 (1987).

*Primary Examiner*—Richard L. Raymond
*Assistant Examiner*—Shailendra Kumar
*Attorney, Agent, or Firm*—Leydig, Voit & Mayer

[57] ABSTRACT

A d- or l-tartaric acid amide derivative serving as a host compound and a method of producing the amide derivative which combines with a guest compound to form a clathrate compound and which is expressed by the following Formula (A) or (B):

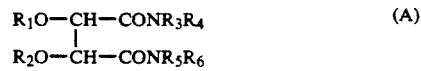

(A)

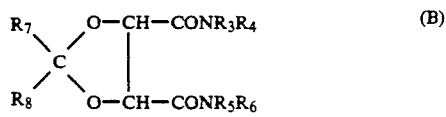

(B)

16 Claims, No Drawings

TARTARIC ACID AMIDE DERIVATIVE AND METHOD OF PRODUCING THE SAME

This application is a continuation of application Ser. No. 07/215,023, filed Jul. 5, 1988, now abandoned.

BACKGROUND OF THE INVENTION

The present invention relates to a tartaric acid amide derivative which is capable of forming clathrate compounds with various organic compounds and to methods of forming such clathrate compounds, particularly with target compounds in the presence of a plurality of compounds.

The inventors have previously clarified that particular types of diamides serving as host molecules take in alcohols and phenols of wide range that serve as guest molecules to form crystals of clathrate compounds.

For example, as such diamide compounds, Japanese Patent Laid-Open Nos. 61-207363 and 61-271235 disclose fumaric acid amide and oxalic acid amide, Japanese Patent Laid-Open No. 61-271267 discloses benzenetricarboxylic acid amide and benzenetetracarboxylic acid amide, and Japanese Patent Laid-Open No. 62-123161 discloses phthalic acid amide, 1,2-cyclohexanedicarboxylic acid amide, $\Delta^4$-cyclohexene-1,2-dicarboxylic acid amide, phenylmalonic acid amide and pyridinedicarboxylic acid amide.

However, each of these diamide compounds exhibits an excellent effect in terms of inclusion, but does not contain any asymmetric carbon atom in itself. Therefore, when these diamide compounds are used with racemic alcohols and phenols for forming clathrate compounds, the clathrate compounds formed have no optical activity. These diamide compounds therefore have no ability to optically resolve racemic modifications.

It is thought that an optically active diamide compound may be synthesized for the purpose of obtaining an optically active clathrate compound. However, this cannot be done easily.

It is well known that a compound which is synthesized by a chemical method alone is generally a racemic modification containing dextrorotatory and levorotatory components in equal quantities and is optically inactive. Since optical resolution is therefore necessary in order to obtain an optically active compound from such a compound, use of such a compound makes the method of obtaining an optically active compound troublesome and economically disadvantageous.

For example, the inventors disclose d- and l-propargyl alcohol derivatives serving as optically active host compounds and a method of producing these compounds in Japanese Patent Laid-Open No. 150526/1983. In other words, a class of propargyl alcohol having the structural formula described below combines with an alkaloid ((-brucine) in a natural form to form a complex, with an optically active clathrate compound in which propargyl alcohol serves as a host compound being crystallized as a result.

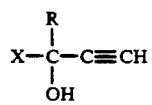

From the so-formed clathrate compound, either a diastereomer of l-brucine and d-propargyl alcohol derivative or a diastereomer of l-brucine and l-propargyl alcohol derivative is crystallized by utilizing the difference in solubility of each according to the reaction conditions. Then, the crystallized diastereomer is decomposed by using an acid to isolate optically active propargyl alcohol derivative.

However, since this method requires the process of synthesizing a racemic modification of the host compound and the subsequent process of optically resolving the racemic modification, the method involves much labor and is troublesome.

The above is also the same with optically active amides which cannot be easily obtained by a method comprising chemical synthesis and optical resolution, and there is no method available which can be put into practical use.

SUMMARY OF THE INVENTION

Accordingly, it is an object of the present invention to provide a tartaric acid amide derivative and a method of producing the same which can solve the above-mentioned disadvantages of the prior art and which comprises simple operations, is superior in economical terms and requires no optical resolution.

It is another object of the present invention to provide a method of isolating a target component from a solution by using an optically active tartaric acid amide derivative.

As a result of the energetic research expended in attempting to achieve the above-described objects, the inventors found that tartaric acid amides have excellent functions as host compounds, leading to the achievement of the present invention.

The inventors have synthesized various amide derivatives by using as raw materials optically pure tartaric acid including the L-compound which originates in nature while accordingly recognizing that no optical change takes place, and investigated the functions of the amide derivatives synthesized as host compounds. As a result, although some degree of specificity to guest compounds was recognized in the amide derivatives, it was found that these derivatives are able to serve as excellent host compounds. More particularly, since large amounts of (-tartaric acid can be obtained at a low price, it was realized to be the most suitable compound for achieving the objects of the present invention.

In other words, the present invention provides derivatives of d- or l-tartaric acid amides expressed by the following Formula (A) or (B):

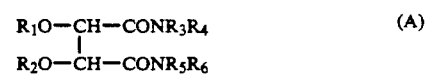

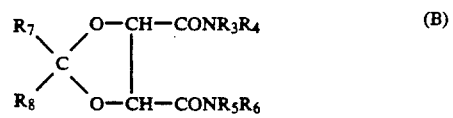

which serve as host compounds to form clathrate compounds with compounds such as alcohols, diols, phenols, aromatic diols, amines, diamines, aldehydes, ketones, carboxylic acids, esters, amides, amino acids and ethers which serve as guest compounds.

In Formula (A) or (B):

$R_1$ and $R_2$ each denotes a straight chain or branched chain primary, secondary or tertiary alkyl group of $C_1$ to $C_{10}$, a straight or branched chain primary, secondary or tertiary aralkyl group of $C_1$ to $C_{10}$, or an alicyclic or aromatic group of $C_5$ to $C_{15}$, $R_1$ and $R_2$ being the same as or different from each other;

$R_3$, $R_4$, $R_5$ and $R_6$ each denotes a straight or branched primary, secondary or tertiary alkyl group of $C_1$ to $C_{10}$, a straight or branched chain primary, secondary or tertiary aralkyl oroup of $C_1$ to $C_{10}$, or an alicyclic or aromatic group of $C_5$ to $C_{15}$, $R_3$, $R_4$, $R_5$ and $R_6$ being the same as or different from each other; and $R_7$ and $R_8$ each denotes a straight or branched primary, secondary or tertiary alkyl group of $C_1$ to $C_{10}$, or a straight or branched chain primary, secondary or tertiary aralkyl group of $C_1$ to $C_{10}$, $R_7$ and R being the same as or different from each other, or the same alicyclic group of $C_5$ to $C_{15}$.

It is required from a structural viewpoint that the tartaric acid amides used in the present invention are able to readily form spatial cavities when clathrate compounds are formed. In view of this requirement, N,N,N',N'-tetrasubstituted tartaric acid amides have the most effective structure. In other words, in Formula (A) or (B), $R_3$, $R_4$, $R_5$ and $R_6$ each denotes a straight or branched primary, secondary or tertiary alkyl group of $C_1$ to $C_{10}$; a straight or branched primary, secondary or tertiary aralkyl group of $C_1$ or $C_{10}$ or an alicyclic or aromatic group of $C_5$ to $C_{15}$; $R_3$, $R_4$, $R_5$ and $R_6$ being the same as or different from each other. Among these groups, a tetracyclohexyl group is the most preferable substituent because tetracyclohexyltartaric acid amide can be easily synthesized and occupies a large space sterically.

In each of the tartaric acid amides that may be used in the present invention, the hydrogen atoms of the hydroxyl groups at the 2- and 3-position are substituted to form an ether bond or a ketal bond. In other words, in Formula (A), $R_1$ and $R_2$ each denotes a straight or branched primary, secondary or tertiary alkyl group of $C_1$ to $C_{10}$ a straight or branched primary, secondary or tertiary aralkyl group of $C_1$ to $C_{10}$; or an alicyclic group or aromatic group of $C_5$ to $C_{15}$; $R_1$ and $R_2$ being the same as or different from each other. In Formula (B), $R_7$ and $R_8$ each denotes a straight or branched primary, secondary or tertiary alkyl group of $C_1$ to $C_{10}$ or a straight or branched primary, secondary or tertiary aralkyl group of $C_1$ to $C_{10}$, $R_7$ and $R_8$ being the same as or different from each other; or the same alicyclic group of $C_5$ to $C_{15}$.

Such host compounds may combine with various compounds as guest compounds such as alcohols, diols, phenols, aromatic diols, amines, diamines, aldehydes, ketones, carboxylic acids, esters, amides, amino acids and ethers to form host-guest compounds, i.e., clathrate compounds. In particular, these host compounds used in the present invention have very good affinity with compounds having hydroxyl groups such as alcohols, diols, phenols and aromatic diols, and can be used for optical resolution of the racemic modifications of aromatic diols substantially with a quantitative yield.

The d- or l-tartaric acid amide derivatives of the present invention are able to form optically active host-guest compounds.

The conditions of the reactions needed for forming such host-guest compounds are described below.

Each of the tartaric acid amide derivatives is mixed with a solution containing the guest compound to be isolated (this solution may be a solution in which the guest compound is dissolved in a solvent or a mixture of the isomers of the guest compound), and the obtained mixture is allowed to stand at room temperature. Consequently, a host-guest compound is crystallized. The molar ratio between a guest compound and each of the tartaric acid amide derivatives is 1 : 0.001 to 1 : 10,000, but molar ratios exhibiting the ability to efficiently crystallize the clathrate compound formed fall within the range of 1 : 0.01 to 1 : 100. The crystallization temperature can be changed, preferably within the range of $-50°$ to $250°$ C., more preferably within the range of $-20°$ to $150°$ C., depending on whether a solvent is present, and, if a solvent is used, the type and amount of the solvent used. However, it is generally satisfactory for the crystallization temperature to be room temperature. If crystallization of a clathrate compound is not easily achievable, the crystallization time of the clathrate compound can be reduced by cooling the reaction solution. There are also cases in which it is desirable to crystallize a clathrate compound at a temperature higher than room temperature for the purpose of increasing the purity of the resulting crystals thereof. It is also effective to use a solvent for the purpose of increasing the crystallization rate or the purity of crystals of a clathrate compound. The time required for crystallization falls within the range of 30 minutes to 20 days, but a long crystallization time within the range of 5 to 20 days cannot be said to be a very favorable operation time for industry. It is therefore preferable to reduce the crystallization time to between 1 hour and 1 day by fully considering the crystallization conditions.

The guest molecules can be isolated from the thus-obtained host-guest compound by various methods such as vacuum distillation, exchange of the host compound or column chromatography.

A description will now be given of examples of a method of producing the tartaric acid amide derivatives of the present invention.

Tartaric acid is essentially a compound which can be optically changed with ease and thus often loses its optical activity during induction to amide compounds.

Therefore, the amidation of optically active tartaric acid generally requires a device of the synthetic operation wherein no optical activity of tartaric acid is lost during the reaction.

A method is reported as an example of such a device in D. Seebach, M. Langer et al., Helv. Chim. Acta, 60, 301 (1977) in which (+)-(R,R)-N,N,N',N'-tetramethyltartaric acid diamide is obtained from (+)-diethyltartaric acid. In this method, (+)-diethyltartaric acid is reacted with dimethylamine to obtain an amide derivative.

However, although this method is a very simple method, it can be applied only to amines with relative low molecular weights and has a narrow application range. For example, when an attempt was made to form an amide derivative by reaction between (+)-diethyltartaric acid and dicyclohexylamine in accordance with the above-described report, this reaction did not proceed.

In addition, when the inventors tested the performance of (+)-(R,R)-N,N,N',N'-tetramethyltartaric acid host compound, this compound resulted in the formation of clathrate compounds with a small number of guest compounds.

On the other hand, the inventors found that tartaric acid can be changed to an amide derivative by forming a ketal bond from the two hydroxyl groups of tartaric acid or a diether bond by introducing substituents into the two hydroxyl groups, without the steric configuration of the two amido groups being changed. In addition, this method was not limited to amines having low molecular weights but could be widely applied.

The most usual method of synthesizing amides is a method in which acid chlorides are reacted with amines. When, therefore, an attempt was made to change the two carboxyl groups of d- or (-tartaric acid into acid chlorides which was then reacted with dicyclohexylamine, this reaction was accompanied with the loss of the optical activity of tartaric acid, and did not allow optically active amide derivatives to be obtained from d- or l-tartaric acid.

Since such a reaction in which d- or l-tartaric acid is directly changed to an acid chloride involves many problems, a method in which tartaric acid is first modified and then changed to an acid chloride has been investigated.

A method has been reported by I. Felher, K. Schenker et al. in Helv. Chim. Acta, 53, 754(1970) in which (+)-2,3-dimethoxysuccinic acid is obtained from (+)-diethyltartaric acid.

Therefore, when the inventors synthesized a dimethyl ether derivative of tartaric acid and then changed the derivative to an acid chloride by an usual method, the optical activity of tartaric acid did not change. It was possible to obtain an amide derivative with a good yield and no loss of the optical activity by reacting the acid chloride produced with dicyclohexylamine.

As a matter of course, it is possible to synthesize a tartaric acid amide by methods other than those described above. For example, a tartaric acid amide can be synthesized by a method in which a tartaric acid derivative is reacted with an amine in the presence of a dehydrating agent or a method in which an amine salt of a tartaric acid derivative is dehydrated by heating.

In addition, tartaric acid amides which are optically pure and expressed by Formula (B) can be obtained by, for example, reacting N,N,N',N'-tetra-substituted tartaric acid diamides such as optically pure N,N,N',N'-tetramethyltartaric acid diamide with compounds such as dimethoxypropane which can introduce ketal bonds into tartaric acid.

DESCRIPTION OF PREFERRED EMBODIMENT

The present invention is described below with reference to examples.

Example 1

5.35 g of (+)-(R,R)-N,N,N',N'-tetramethyltartaric acid amide (I) and 5.5 g of dimethoxypropane were dissolved in 50 ml of benzene, and 0.18 g of p-toluenesulfonic acid monohydrate was added to the obtained solution, followed by heating. After a benzene-methanol azeotrope (b.p. 58° C.) was distilled off from the thus-obtained solution, the solution was cooled to room temperature, neutralized by adding 0.2 g of potassium carbonate thereto, washed with water, and then dried. Benzene was distilled off from the solution under reduced pressure to obtain 5.5 g of (+)-(R,R)-2,3-di-O-isopropylidene-N,N,N',N'-tetramethyltartaric acid amide (II) as a colorless prismatic crystal. The physical properties displayed by this crystal were such that the melting point was 86 to 88° C and the specific rotatory power $[\alpha]_D^{20}$ was +2.5° (C=1.4, CHCl$_3$).

Example 2

1.26 g of the (+)-(R,R)-2,3-di-0-isopropylidene-N,N,N',N'-tetramethyltartaric acid amide (II) obtained in Example 1 and 1.0 g of ( )-10,10'-dihydroxy-9,9'-biphenanthryl (referred to as biphenanthrol (III) hereinafter) were dissolved in 20 ml of ethanol by heating. When the obtained ethanol solution was allowed to stand for 12 hours at room temperature, a colorless prismatic crystal was crystallized. This crystal was recrystallized once from 20 ml of ethanol to produce 0.85 g of a crystal (colorless prismatic crystal) of a clathrate compound containing (+)-(R,R)-2,3-di-O-isopropylidene-N,N,N',N'-tetramethyltartaric acid amide (II) and (−)-biphenanthrol (III) in a ratio of 2 : 2. The physical properties displayed by this crystal were such that the melting point was 178° to 180° C. and the specific rotatory power $[\alpha]_D^{20}$ was −23.9° (CHCl$_3$). When this crystal was dissolved in 5 ml of benzene, and the benzene solution was subjected to silica gel chromatography, 0.48 g of (−)-biphenanthrol (III) was obtained from the benzene eluate. The specific rotatory power $[\alpha]_D^{20}$ of the obtained substance was −54.8° (C=0.5, CHCl$_3$).

On the other hand, the filtrate obtained when the above-described clathrate compound was separated was concentrated under reduced pressure and then purified by silica gel chromatography to obtain 0.49 g of (+)-biphenanthrol which showed a specific rotatory power $[\alpha]_D^{20}$ of +68° (C=0.5, CHCl$_3$).

Example 3

16.8 g of (+)-2,3-di-O-methyltartaric acid (IV) and 41.6 g of phosphorus pentachloride were added to 30 ml of phosphorus oxychloride. In this solution, violent reaction took place while generating a hydrogen chloride gas. After the generation of the gas had moderated, the solution was moderately heated for about 30 minutes (lower than 100° C.). Phosphorus oxychloride was distilled out from the solution under reduced pressure to obtain (+)-2,3-di-O-methyltartaric acid chloride (V) as colorless oil. The obtained acid chloride (V) was dissolved in 50 ml of dried benz and thus-obtained solution was added dropwise under cooling with ice (for about 30 minutes) to 300 ml of anhydrous benzene containing 68 g of dicyclohexylamine which was previously cooled with ice. After the addition had been completed, the solution was agitated for 2 hours, and the temperature thereof was then gradually decreased to room temperature.

After the crystallized dicyclohexylamine hydrochloride had been removed from the solution by suction filtration, the filtrate was washed with dilute hydrochloric acid (3N) water and an aqueous solution of sodium bicarbonate in this order and then dried with anhydrous magnesium sulfate. Benzene was distilled off from the solution to obtain colorless oily (+)-2,3-di-O-methyl-N,N,N',N'-tetracyclohexyltartaric acid diamide (referred to as tartaric acid diamide (VI)).

When the obtained tartaric acid diamide (VI) was allowed to stand at room temperature, crystallization gradually took place. The obtained crystal was recrystallized from petroleum ether to obtain 25 g of a colorless prismatic crystal of (+)-tartaric acid diamide (VI) which showed such physical properties that the melting point was 135° to 140° C. and the specific rotatory power $[\alpha]_D^{20}$ was +57.7° (C=4.0, CHCl$_3$).

Example 4

1.50 g of the (+)-tartaric acid diamide (VI) of Example 3 and 1.27 g (±)-bis-β-naphthol (referred to as binaphthol (VII) hereinafter) were dissolved in 20 ml of ethanol by heating, and the thus-obtained solution was allowed to stand at room temperature for 12 hours, with a colorless prismatic crystal being crystallized.

The obtained crystal was recrystallized from 10 ml of ethanol once to obtain a crystal (colorless prismatic crystal) of a clathrate compound containing the (+)-tartaric acid diamide (VI) and the (−)-binaphthol (VII) in a ratio of 1 : 1. This crystal showed such physical properties that the melting point was 174° to 176° C. and the specific rotatory power $[\alpha]_D^{20}$ was +1.96° (methanol).

This crystal was dissolved in 20 ml of benzene, and the (−)-binaphthol (VII) was extracted with an aqueous solution of 5% sodium hydroxide from the obtained benzene solution. The extract was then acidified with 3N-HCl to obtain 0.34 g of (−)-binaphthol which showed a specific rotatory power $[\alpha]_D^{20}$ of −40.0° (C=1.0, tetrahydrofuran).

The filtrate was concentrated under reduced pressure and then treated in the above-described manner to obtain 0.60 g of (+)-binaphthol which showed a specific rotatory power $[\alpha]_D^{20}$ of +22.3° (C=0.8, tetrahydrofuran).

Example 5

0.58 g of (+)-tartaric acid diamide (VI) and 0.60 g of (±)-1,1'-dihydroxy-spirobifluorenyl (referred to as spirobifluorenol (VIII) hereinafter) were dissolved in 5 ml of ethanol, and thus-obtained solution was allowed to stand for 12 hours at room temperature. The crystal crystallized from the solution was recrystallized once from 5 ml of ethanol to obtain 0.45 g of a crystal (colorless prismatic crystal, m.p. 238 to 243° C.) of a clathrate compound containing (+)-tartaric acid diamide (VI) and (+)-spirobifluorenol (VIII) in a ratio of 1 : 1. The obtained crystal was dissolved in 10 ml of benzene, and (+)-spirobifluorenol (VIII) was extracted with an aqueous solution of 5% sodium hydroxide from the obtained solution. The extract was then acidified with 3N-HCl to obtain 0.22 g of (+)-spirobifluorenol (VIII) which showed a specific rotatory power $[\alpha]_D^{20}$ of +27.1° (C=0.9, methanol).

Example 6

0.53 g of (+)-tartaric acid diamide (VI) and 0.61 g of (±)-3,3'-dihydroxy-4,4'-biphenanthryl (referred to as biphenanthryl (IX) hereinafter) were dissolved in 10 ml of ethanol by heating, and the thus-obtained solution was allowed to stand for 12 hours at room temperature to obtain from the solution a crystal (colorless prismatic crystal, m.p. 224-227° C.) of a clathrate compound containing the (+)-tartaric acid diamide (VI) and the (+)-biphenanthryl (IX) in a ratio of 1 : 1 as a colorless needle-like crystal.

Thus-obtained crystal was dissolved in 10 ml of benzene, and the (+)-biphenanthryl (IX) was extracted with an aqueous solution of 5% sodium hydroxide from the solution. The extract was then acidified with 3N-HCl to obtain 0.33 g of (+)-biphenanthryl (IX) ($[\alpha]_D^{20}$, +5.3° (C=0.7, CHCl₃)).

Example 7

4.06 g of (+)-(R,R)-2,3-di-O-methyl-N,N,N',N'-tetramethyltartaric acid diamide (referred to as tartaric acid diamide (X) hereinafter) and 5.00 g of (±)-binaphthol (VII) were dissolved in 20 ml of benzene by heating, and 5 ml of n-hexane was then added to the thus-obtained solution. The obtained mixture was then allowed to stand for 12 hours at room temperature. The prismatic crystal crystallized from the solution was recrystallized once from the above-described mixed solvent to obtain 3.70 g of a crystal (colorless prismatic crystal, mp. 149-150° C, $[\alpha]_D^{20}$, +61.5° (CHCl₃)) of a clathrate compound containing the (+)-tartaric acid diamide (X) and the (−)-binaphthol (VII) in a ratio of 1 : 1. The obtained crystal was then dissolved in benzene, and the obtained solution was subjected to silica gel chromatography. The benzene eluate was then concentrated to obtain 1.80 g of (−)-binaphthol (VII) which showed a specific rotatory power $[\alpha]_D^{20}$ of −36.6° (C=1.1, tetrahydrofuran).

On the other hand, 2.7 g of (+)-binaphthol (VII) ($[\alpha]_D^{20}$, +21.0° (C=0.55, tetrahydrofuran)) which was obtained by silica gel chromatography of the filtrate obtained when the clathrate compound was separated and 2.19 g of (−)-(S,S)-tartaric acid diamide (X) were dissolved in the above-described mixed solvent, and thus-obtained solution was allowed to stand for 12 hours at room temperature. The crystallized crystal was recrystallized once to obtain 2.70 g of a clathrate compound (colorless prismatic crystal: mp, 150-151° C.; $[\alpha]_D^{20}$, −43.9° (CHCl₃)) containing (−)-tartaric acid diamide (X) and (+)-naphthol (XI) in a ratio of 1 : 1. The obtained crystal was subjected to column chromatography to obtain 1.48 g of (+)-binaphthol (VII) ($[\alpha]_D^{20}$, +36.5° (C=1.3, tetrahydrofuran)).

Example 8

4.80 g of (+)-tartaric acid diamide (VI) and 1.44 g of naphthol (α:β=1 : 1) were dissolved in 10 ml of methanol by heating, and the thus-obtained solution was allowed to stand for 12 hours at room temperature, with 2.3 g of a clathrate compound (colorless needle-like crystal, mp. 199-204° C.) containing tartaric acid diamide (VI) and β-naphthol in a ratio of 1 : 1 being crystallized. When the tartaric acid diamide (VI) was separated from the clathrate compound by column chromatography, 0.53 g of β-naphthol was obtained. (Function and Effect of the Invention)

The tartaric acid amide derivatives used in the present invention combine with various organic compounds serving as guest compounds to form crystals of clathrate compounds.

Although the functional mechanism of each of the host compounds used in the present invention is unclear, in relation to the other host-guest compounds invented by the inventors, it is reasonable to think that the electrical polarization possessed by amido groups functions as attraction force acting between the host and guest compounds and the guest compound is held in a matrix of the spatial cavity formed by two amido groups.

The compounds of to the present invention combine with various organic compounds such as alcohols, diols and phenols which serve as guest compounds to form crystals of clathrate compounds.

The former compounds can be used therefore, as separating and purifying agents for the latter compounds. In particular, the compounds of the present invention which are synthesized from natural tartaric acid serve as optically active host compounds of very low price to form optically active clathrate compounds from racemic alcohols, diols and phenols and thus are industrially useful as optically active compound resolving agents for racemic modifications of these compounds.

Since the tartaric acid amide derivatives are also able to include medicinal and agricultural technical products, such inclusion causes these products to be gradually released, and it is thus possible to prolong the times of potency of these products and to reduce the stimulation thereof.

In addition, since tartaric acid amides are able to include compounds having relatively large molecular weights, it is thought that the tartaric acid amides are widely used as extractants for extracting active components from natural substances.

The present invention enables optical division of aromatic diols such as binaphthol and biphenanthrol from which optically active compounds cannot be easily obtained with good efficiency by a simple prior art by operation.

It is known that optically active binaphthol has the ability to asymmetrically reduce ketones with high yields in combination with lithium aluminum hydride.

This is reported in, for example, Noyori et al., Tetrahedron Lett., 22, 247(1981), Noyori et al., Pure and Appl. Chem., 53, 2315(1981), Noyori et al., J. Am. Chem. Soc., 101, 5843(1979), and Noyori et al., Tetrahedron Lett., 21, 2821(1980).

However, it cannot be easily said that optically active binaphthol is at present sufficiently employed in the industrial field. This is mainly because of the high price of optically active binaphthol which is a major obstacle in industrial employment thereof.

Since the use of the tartaric acid amide derivatives of the present invention enables optically active binaphthol to be obtained with a high yield by a simple operation, it is possible to produce optically active binaphthol at a low price. It is therefore possible to produce with high yields optically active alcohols which are valuable as medicinal and agricultural raw materials by asymmetrical reduction of ketones using the optically active binaphthol. The optical active binaphthol thus brings immeasurable profits to the industrial field.

Similarly, it is also known that biphenanthrol has an effect as an asymmetric reductant which is equal to greater than that of binaphthol. For example, Japanese Patent Laid-Open No. 181033/1985 discloses a method of obtaining (S)-1,2-diphenylethanol with a high yield in which deoxybenzoin is asymmetrically reduced by using lithium aluminum hydride in the presence of optically active biphenanthrol. This method is also not often used industrially due to the availability of biphenanthrol only at a high price. However, since, it is expected that the optically active biphenanthrol may be produced at a low price by using the tartaric acid amide derivatives of the present invention, the industrial employment of the optically active biphenanthrol will be developed in future.

In addition, the tartaric acid amide derivatives are compounds derived from tartaric acid in natural form and are thus compounds exhibiting low degrees of toxicity and high degrees of safety. It is therefore thought that the clathrate compounds obtained by using these compounds as host compounds also exhibit high degrees of safety, and the inclusion by these compounds enables the gradual release of medicines, agricultural chemicals and perfumes and the reduction in the emergent toxicity thereof. Therefore, it must be said that the tartaric acid amide derivatives are very meaningful in the industrial field.

What is claimed is:

1. A method of separating an optically active target component comprising the steps of mixing a d- or l-tartaric acid amide derivative serving as a host compound with a solution comprising a mixture including racemic components, causing said host compound to combine with a guest compound contained in said solution to form a clathrate compound and crystallizing said clathrate compound, said tartaric acid amide derivative being expressed by the following Formula (A) or (B):

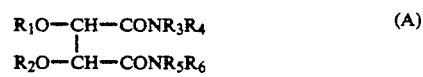
(A)

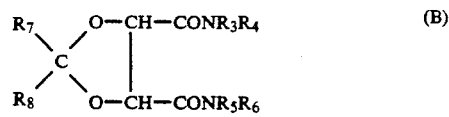
(B)

wherein $R_1$ and $R_2$ each denote a straight chain or branched chain primary, secondary or tertiary alkyl groups of $C_1$ to $C_{10}$, a straight or branched chain primary, secondary or tertiary aralkyl group of $C_1$ to $C_{10}$, or an alicyclic or aromatic group of $C_5$ to $C_{15}$, $R_1$ and $R_2$ being the same as or different from each other; $R_3$, $R_4$, $R_5$ and $R_6$ each denote a straight chain or branched chain primary, secondary or tertiary alkyl groups of $C_1$ to $C_{10}$, a straight or branched chain primary, secondary or tertiary aralkyl group of $C_1$ to $C_{10}$, or an alicyclic or aromatic group of $C_5$ to $C_{15}$, $R_3$, $R_4$, $R_5$ and $R_6$ being the same as or different from each other; and $R_7$ and $R_8$ each denote a straight chain or branched chain primary, secondary or tertiary alkyl groups of $C_1$ to $C_{10}$ or a straight or branched chain primary, secondary or tertiary aralkyl group of $C_1$ to $C_{10}$, $R_7$ and $R_8$ being the same as or different from each other, or the same alicyclic group of $C_5$ to $C_{15}$.

2. A method of separating an optically active target component according to claim 1, wherein the molar ratio between said guest compound and said tartaric acid amide derivative is within the range of 1 : 0.001 to 1 : 10,000.

3. A method of separating an optically active target component according to claim 1, wherein said clathrate compound is crystallized at a temperature within the range of $-50°$ to $250°$ C.

4. A method of separating an optically active target component according to claim 1 wherein said tartaric acid amide derivative is expressed by Formula (A).

5. A method of separating an optically active target component according to claim 1 wherein said guest compound contains one or more functional groups selected from the group consisting of a hydroxyl group, amino group, carbonyl group, and carboxyl group.

6. A method of separating an optically active target component according to claim 1 wherein said guest compound contains at least one hydroxyl group.

7. A method of separating an optically active target component according to claim 6 wherein said guest compound is an alcohol.

8. A method of separating an optically active target component according to claim 6 wherein said guest compound is an aliphatic mono- or diol or an alicyclic mono- or diol.

9. A method of separating an optically active target component according to claim 6 wherein said hydroxyl group-containing compound is a phenol or aromatic diol.

10. A method of separating an optically active target component according to claim 9 wherein said hydroxyl group-containing compound is a binaphthol, biphenanthrol, or spirofluorenol.

11. A method of separating an optically active target component according to claim 1 wherein each of said $R_3$, $R_4$, $R_5$ and $R_6$ are cyclohexyl groups.

12. A method of separating an optically active target component according to claim 1 wherein said tartaric acid amide derivative is (+)-2,3-di-O-methyl-N,N,N',N'-tetracyclohexyltartaric acid diamide.

13. A method of separating an optically active target component according to claim 1 wherein said tartaric acid amide derivative comprises (+)-2,3-di-O-methyl-N,N,N',N'-tetracyclohexyltartaric acid diamide, said guest compound comprises a phenol or aromatic diol, the molar ratio between said guest compound and said tartaric acid amide derivatives is in the range of 1 : 0.001 to 1 : 10000, and said clathrate compound is crystallized at a temperature in the range of −50 to 250° C.

14. A method of separating an optically active target component according to claim 1 wherein said tartaric acid amide derivative is (+)-2,3-di-O-methyl-N,N,N',N'-tetramethyltartaric acid diamide.

15. A method of separating an optically active target component comprising the steps of mixing a d- or l-tarioc acid amide derivative serving as a host compound with a solution comprising a mixture including racemic components comprising at least one of binaphthol, biphenanthrol, and spirofluoroenol, causing said host compound to combine with a guest compound contained in said solution to form a clathrate compound and crystallizing said clathrate compound, said tartaric acid amide derivative being expressed by the following Formula (A) or (B):

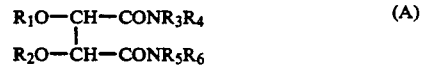

(A)

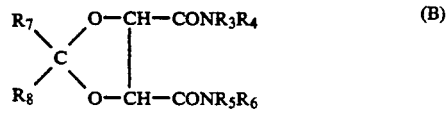

(B)

wherein $R_1$, $R_2$, $R_7$, and $R_8$ each denote a methyl group and $R_3$, $R_4$, $R_5$, and $R_6$, being the same or different, each denote a methyl group or a cyclohexyl group.

16. A method of separating a target component according to claim 15 wherein said tartaric acid amide derivative is expressed by Formula (A).

* * * * *